United States Patent [19]

Hogrefe

[11] Patent Number: 5,016,631
[45] Date of Patent: May 21, 1991

[54] MINIMUM INTERFACE BIOMEDICAL MONITORING SYSTEM

[75] Inventor: Arthur F. Hogrefe, Laurel, Md.

[73] Assignee: The Johns Hopkins University, Baltimore, Md.

[21] Appl. No.: 498,114

[22] Filed: Mar. 23, 1990

[51] Int. Cl.⁵ .............................................. A61N 1/372
[52] U.S. Cl. ................................ 128/419 PS; 128/642
[58] Field of Search ................. 128/419 PS, 630, 631, 128/642, 659, 670, 673, 675, 690, 692, 695, 696, 709, 748, 773

[56] References Cited

U.S. PATENT DOCUMENTS 3,682,160  8/1972  Murata ................................. 128/631
4,794,372 12/1988  Kazahaya ........................ 340/310 A
4,877,032 10/1989  Heinze et al. ........................ 128/695

Primary Examiner—William E. Kamm
Assistant Examiner—Scott M. Getzow
Attorney, Agent, or Firm—Robert E. Archibald; Howard W. Califano

[57] ABSTRACT

The present invention is a universal interface allowing a main implant to supply power and receive data from remotely implanted sensor modules through a minimum number of interconnecting lines. The main module can supply a single DC voltage, two sequentially applied DC voltages or an AC voltage to the sensor module. A capacitor means in the sensor module supplies power while the sensor module is transmitting data.

15 Claims, 1 Drawing Sheet

MINIMUM INTERFACE BIOMEDICAL MONITORING SYSTEM

STATEMENT OF GOVERNMENTAL INTEREST

The Government has rights in this invention pursuant to Contract No. N00039-89-C-5301, awarded by the Department of the Navy.

BACKGROUND OF THE INVENTION

1. Field of the Invention

The present invention is a universal interface allowing a main implant module to supply power to and receive data from remotely implanted sensor modules through a minimum number of interconnecting lines. The remote sensor implants gather useful physiological information from a patient. The main implant could process and telemeter the data to a site remote from the patient or the main module could be an infusion pump or pacemaker that is controlled by the remote sensors.

2. Description of the Prior Art

The benefits of using implantable modules to sense physiological parameters in a patient's or animal's body is well known in the art. Various telemetry transmitters are used to transmit the sensed information to a receiver remote from the body. U.S. Pat. No. 3,682,160 teaches such a miniature medical transmitter to detect a physiological variable and transmit a signal to a receiver placed outside the body. The device is an orally swallowable miniature transmitter for measuring pH values that is powered by the remote receiver.

The prior art does not teach multiple implantable sensor modules coupled to a main implant module. However, outside the area of medical arts remote sensors and central processor modules are taught. U.S. Pat. No. 3,603,946 teaches an electrical means that is switched from a high to a low impedance state by a control signal. A capacitor is used to hold the electrical switch means in its low impedance state until switched. U.S. Pat. No. 4,794,372 teaches a two-wire DC signal telemetering system. The receiving station receives signals and provides operating power along two wires from a sensor that measures a variable, such as temperature or flow rate. U.S. Pat. No. 3,501,132 also describes techniques for transmitting power and information over common wires.

SUMMARY OF THE INVENTION

The present invention provides an interface between a main implant and one or more implanted sensor modules. The main implant could contain signal processing and communications used to telemeter information from the patient's body or it could comprise an infusion pump or pacemaker or similar electronic apparatus for providing a physiological stimulus. The sensor module may be any transducer or chemical sensor that can be used to measure a useful physiological parameter in the patient's body.

Since the main module and sensor modules are implanted in a patient's body, they are exposed to a rather harsh biomedium. The implants are usually encased in a durable substance that is biocompatible, such as titanium. For an interface to operate optimally the design must be such that a minimum number of wires penetrate through the case of the implant modules. In addition, the interface to be designed optimally must have a minimum number of lines interfacing and these lines must be able to: (1) supply power to the remote sensor's processing electronics; and (2) provide an information output channel from the sensor module to the main module.

The unique design of the present invention accomplishes each of the above design criteria. The invented interface only requires two leads per sensor module. One of these leads is grounded to the case so that only a single lead per sensor module need penetrate through the case of the main implant module. This unique interface can power the sensor module with either: (1) a single DC voltage; (2) two sequentially applied DC voltages; or (3) an AC voltage, that can be converted by a sensor module to a DC voltage or voltages as necessary. An electronic switching means, such as a FET switch, is used to convert the two leads from the powering phase where voltage and power are supplied to the sensor module to a reading phase where the same leads are used as a communication link between the sensor module and the main implant.

A basic embodiment of the invention generally includes: a power source located in the main module, first and second wires running from the main implant module to a particular sensor module, the first wire being connected to ground, a switching means located in the main implant for selectively connecting such second wire to said power source during a powering phase, electronics located in said main implant during the reading phase, a sensor means located in the sensor module for detecting physiological parameter, processing electronics external to said central module and operably coupled to said sensor providing a current, I, along the second wire that is functionally related to the sense physiological parameter, a capacitor means located in the sensor module and positioned across said first and second wires, that is the charge during a powering phase and for providing power to and processing electronics during the reading phase and, the diode means located in the sensor module for disconnecting said capacitor from said second line during the reading phase.

DETAILED DESCRIPTION OF THE PREFERRED EMBODIMENTS

Figure 1:
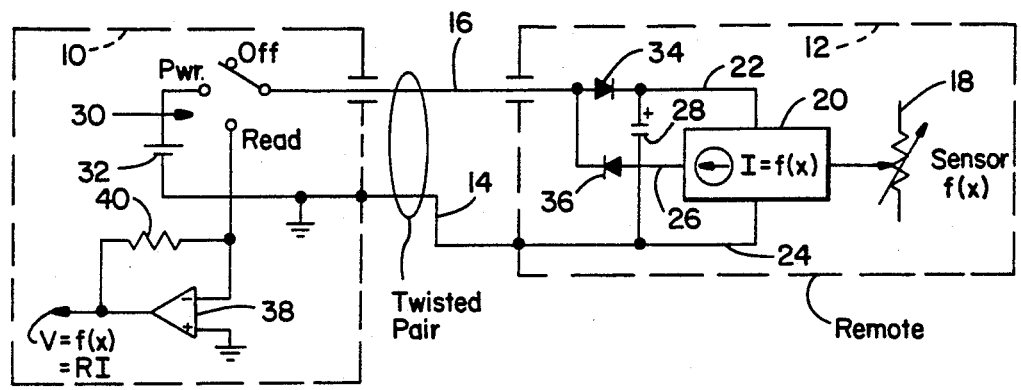
FIG. 1 is a schematic drawing of the invented interface showing an embodiment for providing a single level of voltage to power the sensor module and receive data from the sensor module.

The most basic embodiment of the apparatus, which is shown in FIG. 1, comprises: a main implant 10, and a plurality of implanted sensor modules 12, only one of which is shown. The main implant could contain signal processing and communication electronics used to telemeter sensor information to a site remote from the body or it could comprise an infusion pump or pacemaker or similar electronic apparatus for providing a physiological stimulus in response to the sensor input. Each sensor module is connected to the main implant 10 by a ground wire 14 and a signal wire 16. The ground wire 14 can be connected to the metallic enclosure surrounding the main implant. Only the sensor wire 16 need penetrate through the case of the main implant. Therefore, the invention only requires a single line to penetrate the case of the main implant for each sensor module.

Each sensor module 12 will contain its own signal processing electronics and therefore must be supplied power. The signal processing will perform some level of initial signal analysis and provide as an output a current level, I, the level of which is indicative of the magnitude of the measured perimeter. Therefore, the interface between the sensor module and the main module must meet two requirements: (1) it must supply power to the sensor module; sensor, and (2) it must provide an information output channel from the sensor module to the main module.

The sensor 18 may be any transducer or chemical sensor that can be used to measure a useful physiological parameter in the patient's body. A nonlimiting example of typical sensors would be: (1) a strain gauge connected to muscle tissue that produces a varying impedance; (2) a semiconductor pressure module that produces a varying capacitance when exposed to pressure changes; (3) direct electrical pickups to detect electrical activity in muscle tissues or the heart and produce a voltage signal, or (4) chemical sensors responsive to certain chemicals of physiological importance, such as glucose.

The sensor 18 is connected to signal processing electronics 20, which generates an output current, I, as a function of variations in signal parameters, X, as defined by sensor 18. The signal processing electronics receives power voltage along lines 22 and 24 and provides an output current signal (I) along line 26. The power to lines 22 and 24 are supplied by capacitor 28, as long as sufficient charge remains on the capacitor. To charge the capacitor 28, switch 30 in the main implant is turned to the "power" setting, thereby permitting current flow from the battery 32 along interface lead 16 through diode 34 to capacitor 28 and then returning to ground by ground lead 14. The current is applied for a set time to assure that the capacitor 28 is charged and that the signal processing electronics 20 is stable and functioning. During this cycle, diode 36 is reversed biased and appears as an open circuit. After the charging operation is completed, which may take 2 to 10 milliseconds, switch 30 is turned to the "read" position allowing the signal current, I, to pass through diode 36 and along line 16 to the op-amp 38 and therefore to resistor 40 which provides an output signal voltage V = F(X) = RI. While in the "read" mode, capacitor 28 supplies power sufficient to operate the signal processing electronics 20. While switch 30 is in the "read" position it puts a virtual ground on line 16. This drops the voltage on line 16 and line 26 to ground. Diode 34 becomes reversed biased and therefore is an open circuit. The signal processing electronics 20 provides a constant current source which causes the current (I) to pass through diode 36 and via line !6 into the virtual ground of amp 38. The output from the op-amp 38 is a voltage level, V, which is proportional to the current (I) that is coming from the sensor electronics 20 and the feedback resistor 40 (i.e., V=RI).

Each sensor module 12 could have the following cycle: First, the particular sensor would be "off" while the other sensor modules are being accessed. Each sensor module may be accessed once per second. Secondly, the switch could be turned to the "power" setting, so that the particular sensor could be powered for a short length of time prior to data acquisition. This period may range from 2-10 milliseconds until capacitor 28 is charged and the signal processing electronics has stabilized. Thirdly, the switch is turned to the "read" mode and current from the sensor module is "read" while capacitor 28 powers the sensor module electronics.

Figure 2:
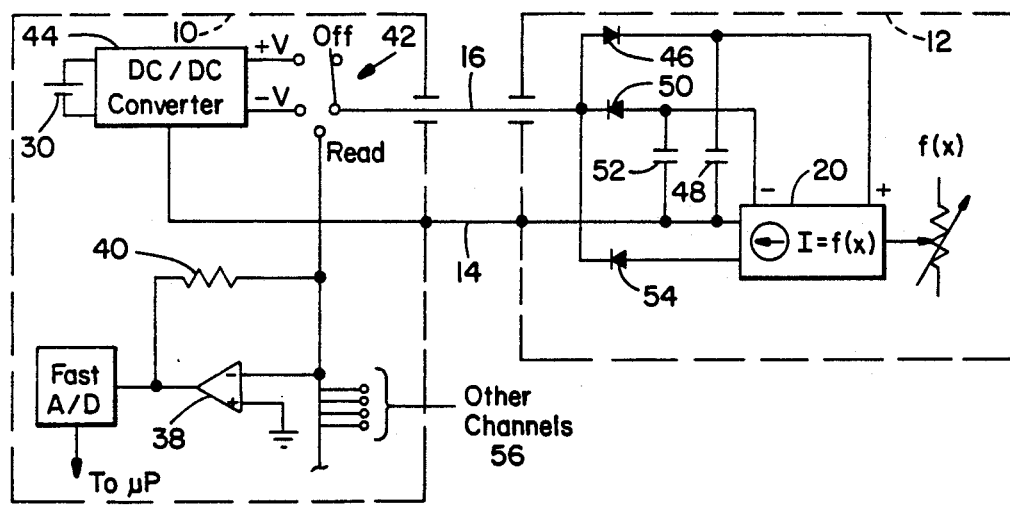
FIG. 2 is a schematic drawing of the invented interface showing an embodiment for providing two levels of voltage to power the sensor module and receive data from the sensor module.

FIG. 2 is a more complex embodiment of the present invention which allows the power supplied to the sensor module 12 to be at a voltage level higher than that supplied by battery 30 internal to the main implant 10. This embodiment also enables multiple power levels to be generated at the main implant module 10 if that is required by the various sensor modules 12 connected to it. This is accomplished by having the selector switch 42 switch sequentially between two or more voltage levels.

When switch 42 is positioned in the "V+" setting, the voltage from the DC/DC converter 44 will pass through diode 46 and charge capacitor 48 with a significant positive voltage relative to ground. When switch 42 is positioned in the "V−" setting, the voltage from the DC/DC converter 44 will pass through diode 50 and will charge capacitor 52 with a significant negative voltage relative to ground. The output current (I) supplied by the sensor module signal processor electronics 20 must be small enough that it would have no effect on the power supply 30 located in the main implant 10; because when switch 42 is set to the "V−" setting the output current, I, is shorted to the negative voltage of the power supply. When switch 42 is moved to the "read" position, line 16 is connected to virtual ground and as a result diodes 46 and 50 will be reversely biased and will form an open circuit. Diode 54 will appear "closed" and will permit the output current, I, supplied by the sensor module electronics to pass through the op-amp 38 and provide an output voltage (V=IR, where R is feedback resistor 40). During the "read" cycle, capacitor 52 will carry a significant negative voltage and capacitor 48 will carry a significant positive voltage. This voltage will be used to drive the sensor unit's signal processing electronics 20 during the "read" cycle. Capacitor 52 may be charged to a typical negative voltage of −5 volts, and capacitor 48 may be charged to the typical positive voltage of +5 volts; so, when diodes 46 and 50 have become reverse bias the capacitor can supply 10 volts to the sensor unit signal processing electronics. In addition, with input lead 16 connected to virtual ground, the voltage supplied by the capacitors will reverse bias diodes 46 and 50 so they will be "open circuit".

As shown in FIG. 2, the main implant 10 can have a number of channels shown by lines 56, with each channel connected to a different sensor module. With this invention only one wire per channel is needed to pass through the implant case. The switch 42 could be an array of FET switches, with each switch connected to a different channel. In that way, the single implant power source 44 could be used to sequentially power each sensor module. The FET array would be programmed with a sequence requiring the main implant to power, command, and obtain telemetry information from each of the sensor modules. The FET switch associated with a particular channel would also be programmed to deliver the power along line 16 to the particular sensor module. In this way, the main implant 10 can be of general purpose, and is independent of the design requirements for each sensor module and can interface with a number of different sensor modules each having different power and voltage requirements. The only design limitation is that each sensor module must output a constant current, I, indicative of the sensed parameter.

Figure 3:
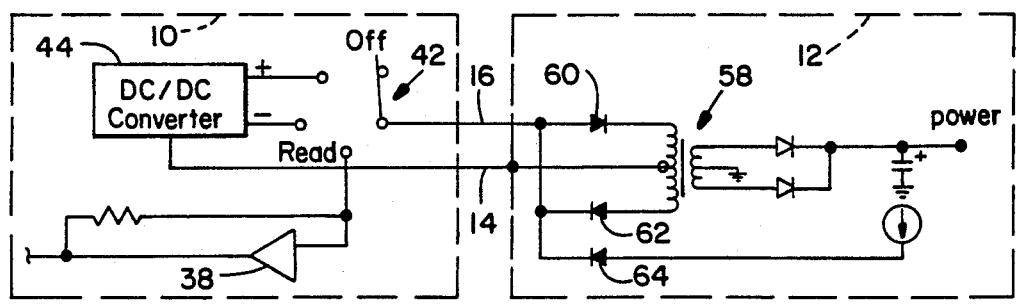
FIG. 3 is a schematic drawing of the invented interface showing an embodiment for providing an AC drive power to the sensor module and receiving data from the sensor module.

In FIG. 3, this invention is extended further, providing more versatility in the level of power supplied to the sensor module electronics. In this embodiment, the FET switch 42 is toggled between plus (+) and negative (−) voltage supplied by the DC/DC converter 44. This will provide an AC signal along line 16 if for instance the FET switch has a 20 KHz chopping rate. This AC signal can be converted to any voltage level by a transformer 58 located in the sensor module. Utilizing transformer coupling, the sensor module can provide any desired voltage. Diode 60 allows current to pass through the primary windings of the transformer in a clockwise direction, and diode 62 allows current to pass through the windings in a counter clockwise direction. Diode 64 isolates the signal processing electronics and allows the sensor current signal, I, to run via line 16 to the op-amp 38 when switch 42 is in the "read" position. The transformer could be used to convert the lower voltage provided by the main implant battery to a much higher voltage for use by a particular sensor module. The transformer 58, shown in FIG. 3, would connect to a rectified circuit and store power in a capacitor for use by the sensor electronics, as was taught in FIGS. 1 and 2. The transformer 58 could have multiple output windings so several different voltages could be used to power the sensor electronics. Therefore, FIG. 3 provides an interface between the main implant 10 and the sensor module 12 which accommodates both AC power and telemetry along the same two interface lines.

It is envisioned that a given application could have all three circuits shown in FIGS. 1, 2 and 3. The only difference would be whether the FET switch 42 applies power from a single voltage line, as in FIG. 1, or alternates between two stable voltage levels as in the FIG. 2 embodiment, or cycles rapidly between two voltage levels thereby generating an AC drive power as taught in FIG. 3. The FET would be programmed differently for different sensor channels. One sensor module may require only a single drive voltage whereas another may require an AC drive. In essence, the invention allows any number of sensor modules, X, to be powered by and to communicate with the main module. The interface only requires that X leads run through the case with one ground lead connected to the case.

The present invention provides excellent noise immunity. The sense lead and ground lead would generally form a twisted pair to keep noise to a minimum. During the time a particular sensor is being "read" the sense line is at the same voltage as the ground line to minimize leakages between the ground lead and the sense line should insulation failure be caused by the bio-medium. Therefore, the invented apparatus can afford to have a low "read" out current, I, supplied by the sensor module without fear of receiving a disrupted or unintelligeable signal.

Obviously, many modifications and variations of the present invention are possible in light of the above teachings. It is therefore to be understood that within the scope of the appended claims the invention may be practiced otherwise than as specifically described.

What is claimed is:

1. An electrical apparatus for a main implant module interfaced with at least one implant sensor module, comprising:
   a power source located in the main implant module;
   first and second wires running from the main implant module to a particular sensor module, said first wire connected to ground;
   a switching means located in the main implant for selectively connecting said second wire to said power source during a powering phase and to electronics located in said main implant during a reading phase;
   a sensor means located in the sensor module for detecting a physiological parameter;
   processing electronics internal to said sensor module and operably coupled to said sensor means for providing a current, I, along the second wire to the electronics located in said main implant, said current I being functionally related to the sensed physiological parameter;
   a capacitor means located in the sensor module and positioned across said first and second wires that is charged during the powering phase and for providing power to said processing electronics during the reading phase; and
   a diode means located in the sensor module for disconnecting said capacitor from said second line during the reading phase.

2. The apparatus of claim 1, wherein said second wire is coupled to virtual ground during said reading phase.

3. The apparatus of claim 1, wherein said electronics located in the main module comprises an op-amp and feedback resistor.

4. The apparatus of claim 1, further comprising a second diode means located in the sensor module for protecting the processing electronics during the powering phase.

5. An electronic apparatus for a main implant module interfaced with at least one implant sensor module, comprising:
   a power source located in the main implant module having "$V^{30}$" and "V−" outputs;
   first and second wires running from the main implant module to a particular sensor module, said first wire connected to ground;
   a switching means located in the main implant for selectively connecting said second wire to "V+" and then to "V−" during a powering phase and to electronics located in said main implant during a reading phase;
   a sensor means located in the sensor module for detecting a physiological parameter;
   processing electronics internal to said sensor module and operably coupled to said sensor means for providing a current, I, along the second wire to the electronics located in said main implant, said current I being functionally related to the sensed physiological parameter; and,
   two capacitor means, each capacitor means connected by oppositely biased diodes between said first and second wires, said capacitors being charged during the powering phase, for providing power to said processing electronics during the reading phase.

6. The apparatus of claim 5, wherein said second wire is coupled to virtual ground during said reading phase.

7. The apparatus of claim 5, wherein said electronics located in the main module comprises an op-amp and feedback resistor.

8. The apparatus of claim 5, further comprising a second diode means located in the sensor module for protecting the processing electronics during the powering phase.

9. The apparatus of claim 5, wherein each capacitor means in said two capacitor means is charged with opposite polarity from the other capacitor means and is coupled in series with the other capacitor means to supply power to said processing electronics.

10. An electronic apparatus for a main implant module interfaced with at least one implant sensor module, comprising:
   a power supply located in the main implant module having "V+" and "V−" outputs;
   first and second wires running from the main implant module to a particular sensor module, said first wire connected to ground;
   a switching means located in the main implant for selectively connecting said second wire across "V+" and "V−" to generate an alternating current across said first and second wires during a powering phase and to electronics located in said main implant module during a reading phase;
   a sensor means located in the sensor module for detecting a physiological parameter;
   processing electronics internal to said sensor module for producing a current, I, along the second wire to the electronics located in said main implant, said current I being functionally related to the sensed physiological parameter;
   a means in the sensor module for converting the alternating current supplied by said first and second wire into a dc voltage that is stored in a capacitor means.

11. The apparatus of claim 10, wherein said means for converting involves a transformer with primary wires coupled to said first and second wires through opposed biased diodes, whereby the "V+" runs through the primary winding in one direction and the sequentially applied "V−" runs through primary winding in the opposite direction.

12. The apparatus of claim 11, wherein the secondary of said transformer is connected to a rectifier circuit to generate a d.c. voltage, wherein said d.c. voltage is stored in said capacitor means during the reading phase.

13. The apparatus of claim 10, wherein said second line is coupled to virtual ground during said reading phase.

14. The apparatus of claim 10, wherein said electronics located in the main module comprises an op-amp and feedback resistor.

15. The apparatus of claim 10, further comprising a diode means located in the sensor module for protecting the processing electronics during the powering phase.

* * * * *